US008412030B2

(12) United States Patent
Béland et al.

(10) Patent No.: US 8,412,030 B2
(45) Date of Patent: Apr. 2, 2013

(54) METHOD AND APPARATUS FOR DISPENSING A FRAGRANCE

(75) Inventors: René Maurice Béland, Waterford, WI (US); Nitin Sharma, Kenosha, WI (US); Deliang Shi, Racine, WI (US); John R. Wietfeldt, Franksville, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 781 days.

(21) Appl. No.: 12/548,158

(22) Filed: Aug. 26, 2009

(65) Prior Publication Data

US 2011/0049259 A1    Mar. 3, 2011

(51) Int. Cl.
F24F 6/08  (2006.01)

(52) U.S. Cl. .................... 392/395; 392/386; 392/394

(58) Field of Classification Search .......... 392/386–406, 392/324–337; 237/78; 4/524–537
See application file for complete search history.

(56) References Cited

U.S. PATENT DOCUMENTS

| | | |
|---|---|---|
| 2,562,960 A | 8/1951 | Stern |
| 2,597,195 A | 5/1952 | Smith |
| 4,284,132 A | 8/1981 | Strand, Sr. |
| 4,603,030 A | 7/1986 | McCarthy |
| 5,023,020 A | 6/1991 | Machida et al. |
| 5,259,062 A | 11/1993 | Pelonis |
| 5,297,988 A | 3/1994 | Nishino et al. |
| 5,565,148 A | 10/1996 | Pendergrass, Jr. |
| 6,783,117 B2 | 8/2004 | Wohrle |
| 6,790,408 B2 | 9/2004 | Whitby et al. |
| 7,223,361 B2 | 5/2007 | Kvietok et al. |
| 7,344,123 B2 | 3/2008 | Pankhurst et al. |
| 7,493,028 B2 | 2/2009 | DeWitt et al. |
| 2005/0281718 A1 | 12/2005 | Echevarria |
| 2006/0188238 A1* | 8/2006 | Kent .............................. 392/394 |
| 2007/0163772 A1* | 7/2007 | Bhatti et al. ................... 165/202 |
| 2007/0280653 A1* | 12/2007 | Viera ............................. 392/395 |

FOREIGN PATENT DOCUMENTS

| | | |
|---|---|---|
| WO | 03028775 A1 | 4/2003 |
| WO | 2004093929 A2 | 11/2004 |
| WO | 2005092400 A1 | 10/2005 |
| WO | 2005106344 A2 | 11/2005 |
| WO | 2006004891 A1 | 1/2006 |
| WO | 2006074562 A1 | 7/2006 |
| WO | 2009085170 A1 | 7/2009 |

OTHER PUBLICATIONS

PCT/US2010/002345 International Search Report Dated Feb. 25, 2011.

* cited by examiner

*Primary Examiner* — Thor Campbell (57) ABSTRACT

A method of dispensing a volatile active into the surrounding environment includes the steps of providing a fragrance dispenser having a housing, a fan disposed within the housing and having a airflow director, first and second chambers disposed within the housing, and first and second fragrances disposed in the first and second chambers. The first and second chambers include first and second shutters covering first and second outlets, and first and second heaters, respectively. The method further includes the steps of activating the first heater to volatilize the first fragrance for a first time period, simultaneously activating the fan and the opening the first shutter to dispense the volatilized first fragrance from the first chamber into the surrounding atmosphere, activating the second heater to volatilize the second fragrance for a second period of time, and simultaneously activating the fan and opening the second shutter to dispense the volatilized second fragrance from the second chamber into the surrounding atmosphere.

15 Claims, 11 Drawing Sheets

METHOD AND APPARATUS FOR DISPENSING A FRAGRANCE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

FIELD OF THE DISCLOSURE

The present disclosure generally relates to a volatile material dispensing apparatus and a method of dispensing volatile materials, and more particularly to a dispensing apparatus and method that increase user perception of the volatile materials.

BACKGROUND OF THE DISCLOSURE

It is known that a user's perception of a dispensed fragrance of a constant intensity tends to decay over time. This decay in perception, which is commonly referred to as adaptation and/or habituation, reduces the user's enjoyment of the dispensed fragrance. It is generally believed that adaptation and/or habituation can be reduced by changing the level of intensity of the dispensed fragrance or by dispensing a different fragrance. Fragrance dispensers and methods of dispensing fragrances that address the issue of adaptation and/or habituation are known in the art. Such fragrance dispensers may require significant power resources to operate depending on the electrical requirements for the operation of a heat source and/or fan (if either/both are being used within the fragrance dispenser).

One such fragrance dispenser includes an apparatus that is capable of dispensing one or more fragrances through an aroma delivery device. The delivery device includes a housing having an air passage extending therethrough. The aroma delivery device is disposed in a receptacle that is attached to the housing, wherein a plurality of aroma-bearing elements each containing a volatile material is disposed within a reservoir. A diffusion rate-controlling structure surrounds the reservoir and allows for permeation of the volatile material at a controlled rate. A pressurized air source sends air through the air passage and through the aroma-bearing element that is disposed within the passage, such that fragranced air passes through the air passage and through an outlet to the surrounding environment.

Another dispenser includes a housing having a plurality of scent-filled cartridges disposed within pockets formed in the housing. Each of the cartridges includes an actuating structure whereby, when pressure is exerted thereon, the cartridge is opened and scent therein is diffused into the dispenser. Each pocket includes a heating member disposed therein such that the heating member is below the cartridge when a cartridge is inserted therein to volatize a respective scent. The housing further includes a fan that generates air flow that entrains the diffused scent and pushes same through an opening formed in the housing into a surrounding atmosphere.

Yet another dispenser emits fragrances in an alternating sequence while the dispenser is activated. The dispenser includes, for example, first and second heaters for emitting first and second fragrances, respectively. In one embodiment, the fragrances are alternately emitted by deactivating one of the heaters at the same time the other of the heaters is activated. Alternatively, one of the heaters may be deactivated followed by a gap period and then the other of the heaters may be activated. Still further, one of the heaters may be activated before the other of the heaters is deactivated to create an overlap period.

SUMMARY OF THE INVENTION

According to one aspect of the present disclosure, a method of dispensing a volatile active into the surrounding environment includes the steps of providing a fragrance dispenser having a housing, a fan disposed within the housing and having a airflow director, first and second chambers disposed within the housing, and first and second fragrances disposed in the first and second chambers. The first and second chambers include first and second shutters covering first and second outlets, and first and second heaters, respectively. The method further includes the steps of activating the first heater to volatilize the first fragrance for a first time period, simultaneously activating the fan and the opening the first shutter to dispense the volatilized first fragrance from the first chamber into the surrounding atmosphere, activating the second heater to volatilize the second fragrance for a second period of time, and simultaneously activating the fan and opening the second shutter to dispense the volatilized second fragrance from the second chamber into the surrounding atmosphere.

According to another aspect of the present disclosure, a method of dispensing a volatile material into the surrounding environment includes the steps of providing a fragrance dispenser having a housing, a fan disposed within the housing and having a airflow director, first and second chambers disposed within the housing, and first and second fragrances disposed in the first and second chambers. The first and second chambers include first and second shutters covering first and second outlets, and first and second heaters, respectively. The method also includes the step of activating the first heater to volatilize the first fragrance disposed within the first chamber, wherein the first shutter is closed so as to not allow fragrance to escape from the first chamber. The first heater is maintained in the activated state for a first period of time and deactivated. The first shutter is opened to allow the flow of fragrance-laden air out of the first chamber and the fan is positioned to direct airflow through the first chamber. The fan is activated for a second period of time, deactivated, and the first shutter is closed to prevent airflow out of the first chamber. The second heater is activated to volatilize the second fragrance disposed within the second chamber and the second shutter is closed so as to not allow fragrance to escape from the second chamber. The second heater is in the activated state for a third period of time and then deactivated. The second shutter is opened to allow the flow of fragrance-laden air out of the second chamber and the fan is positioned to direct airflow through the second chamber. The fan is activated for a fourth period of time and deactivated. The second shutter is closed to prevent airflow out of the second chamber.

According to yet another aspect of the present disclosure, an apparatus for dispensing a volatile active into the surrounding environment includes a housing having first and second chambers, a fan disposed within the housing, and an airflow director disposed adjacent the fan for directing airflow into only one of the first or second chambers at a time. The apparatus further includes first and second containers having first and second fragrances disposed therein and first and second wicks in communication with the first and second fragrances and extending into the first and second chambers, respectively, wherein the first and second inserts are disposed in a central portion thereof. First and second heaters are disposed adjacent the first and second inserts to transfer heat to the first and second inserts, respectively.

BRIEF DESCRIPTION OF THE DRAWINGS

Other aspects and advantages of the present disclosure will become apparent upon consideration of the following detailed description, wherein similar structures have similar reference numbers.

DETAILED DESCRIPTION

An illustrative volatile material dispenser 50 is shown in FIGS. 1-6, 7A, and 7B. The dispenser 50 generally includes a housing 52, a fan 54 (FIGS. 2-6, 7A, and 7B) disposed within the housing 52, and first and second containers 56a, 56b containing volatile material and disposed in the housing 52.

Figure 4:
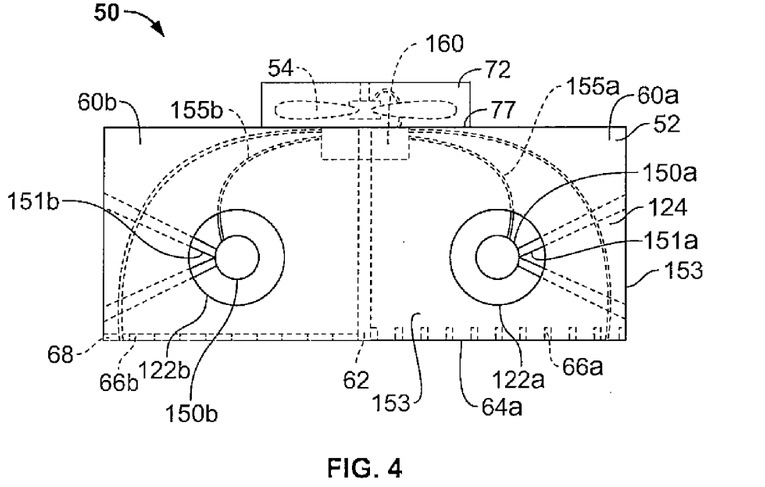
FIG. 4 is a bottom plan view of the apparatus of FIG. 1.
Figure 6:
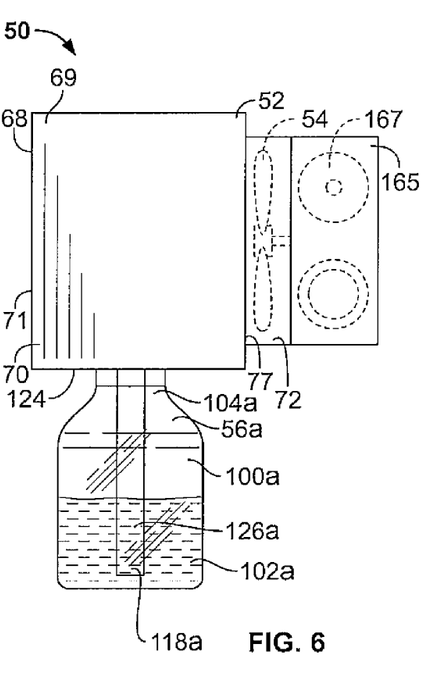
FIG. 6 is a side elevational view of the apparatus of FIG. 1 with batteries for powering the apparatus.
Figure 7A:
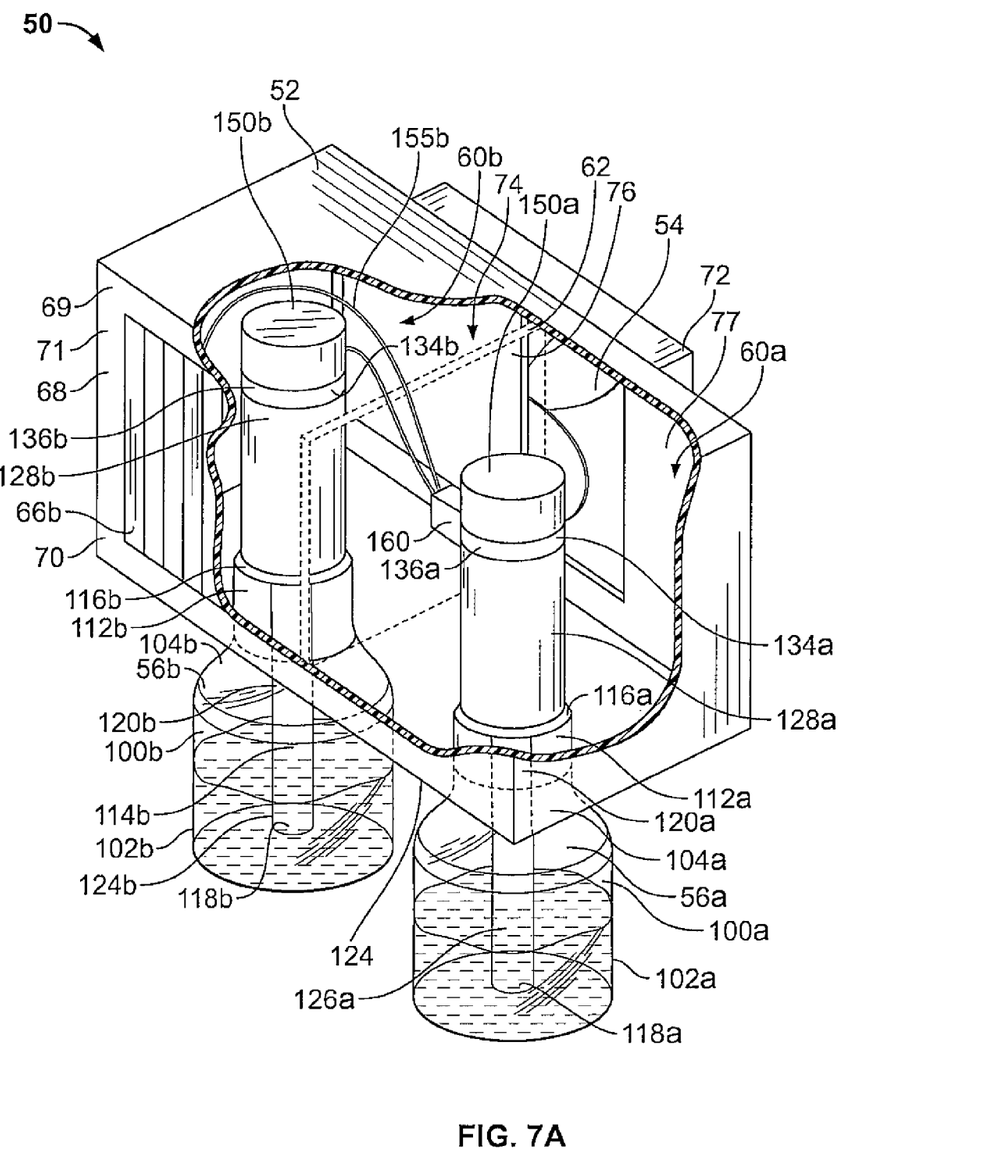
FIG. 7A is a top isometric view of the apparatus of FIG. 1 with a portion of the front and side thereof removed and incorporating a first airflow director.
Figure 7B:
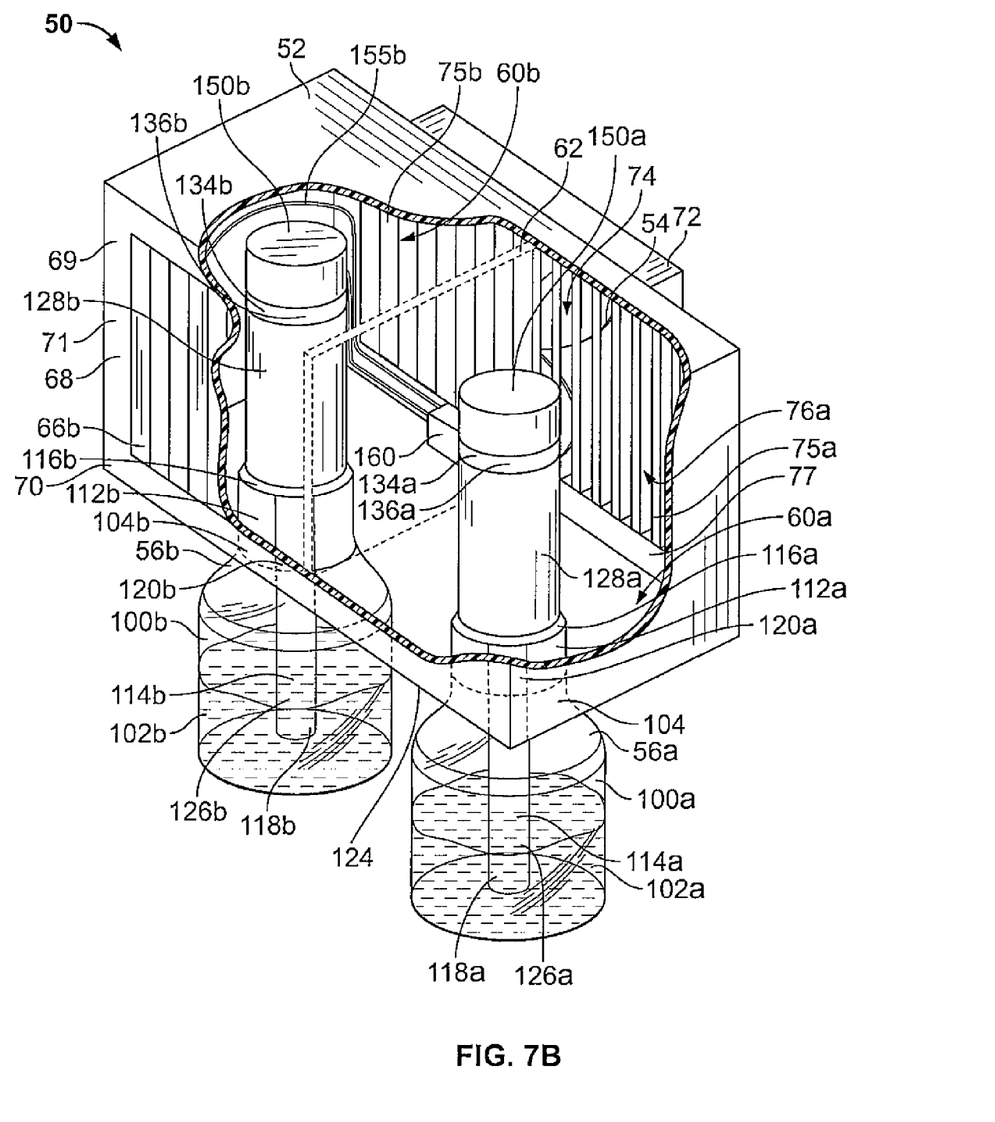
FIG. 7B is a top isometric view of the apparatus of FIG. 1 with a portion of the front and side thereof removed and incorporating a second airflow director.

Referring again to FIGS. 1-6, 7A, and 7B, the housing 52 is divided into first and second chambers 60a, 60b with a dividing wall 62 forming the chambers 60a, 60b and acting as a barrier to prevent airflow between the chambers 60a, 60b. The first and second containers 56a, 56b are disposed within and associated with respective chambers 60a, 60b. Although two chambers 60a, 60b and containers 56a, 56b are depicted, two or more chambers 60a, 60b and containers 56a, 56b may be utilized. Each chamber 60a, 60b includes an outlet 64a, 64b, respectively, to allow volatile material to be diffused therethrough. Although the chambers 60a, 60b are depicted as being substantially rectangular in shape, any shape and/or size chambers 60a, 60b that would enable the method of the present disclosure are possible. One or more of the interior walls 63 of the chambers 60a, 60b may be lined with a material 61 that prevents absorption of the volatile material into the interior walls 63. The material 61 may cover a portion of one or more of the walls 63, as shown in FIG. 7, or may cover the entirety of one or more of the walls 63 of the chambers 60a, 60b, as depicted in FIG. 4. The material 61 preferably substantially prevents absorption of volatile material by one or more of the walls 63 and comprises a metal, alloy, or heat resistant polymer, for example, aluminum, copper, polytetrafluoroethylene (Teflon®), and the like. The material 61 may be the same for each interior wall 63 of an individual chamber 60a, 60b, or the interior walls 63 of an individual chamber 60a, 60b may be different. If both chambers 60a, 60b are coated with the material 61, the materials 61 utilized in the chambers 60a, 60b may be the same or different.

Figure 1:
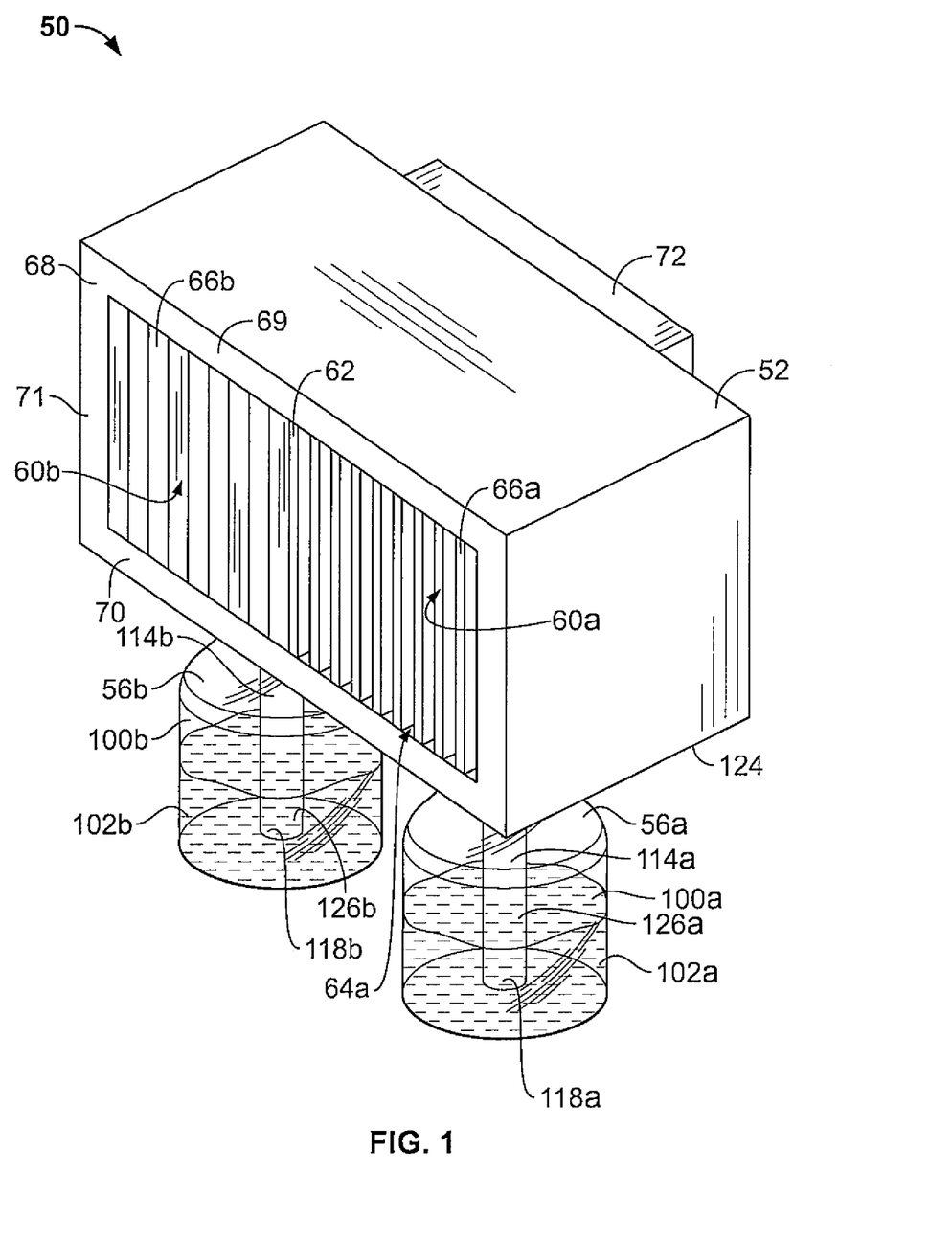
FIG. 1 is a top isometric view of an apparatus for dispensing volatile actives.
Figure 2:
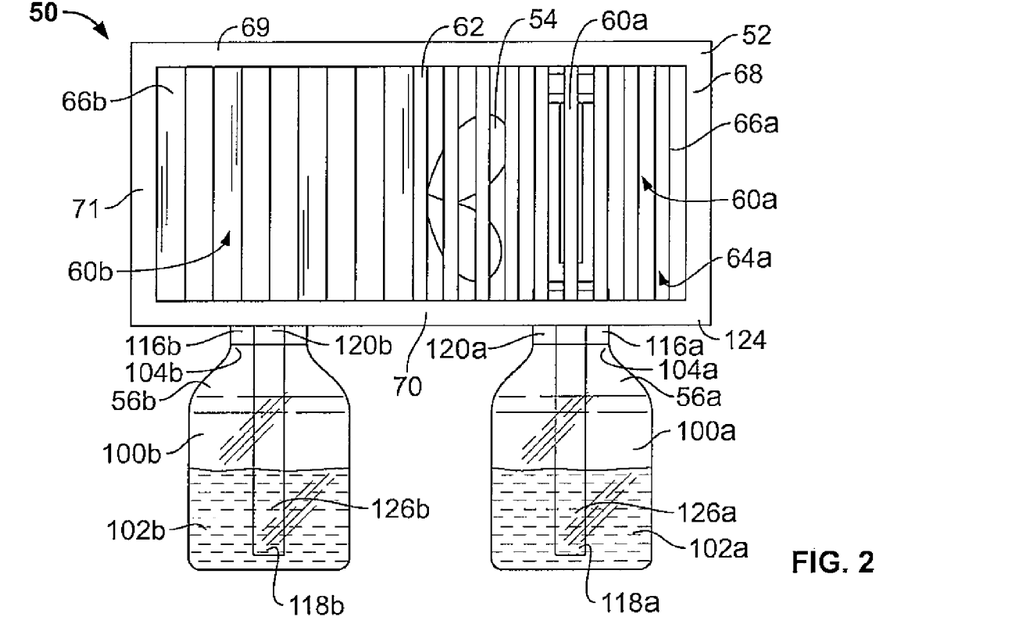
FIG. 2 is front elevational view of the apparatus of FIG. 1.
Figure 3:
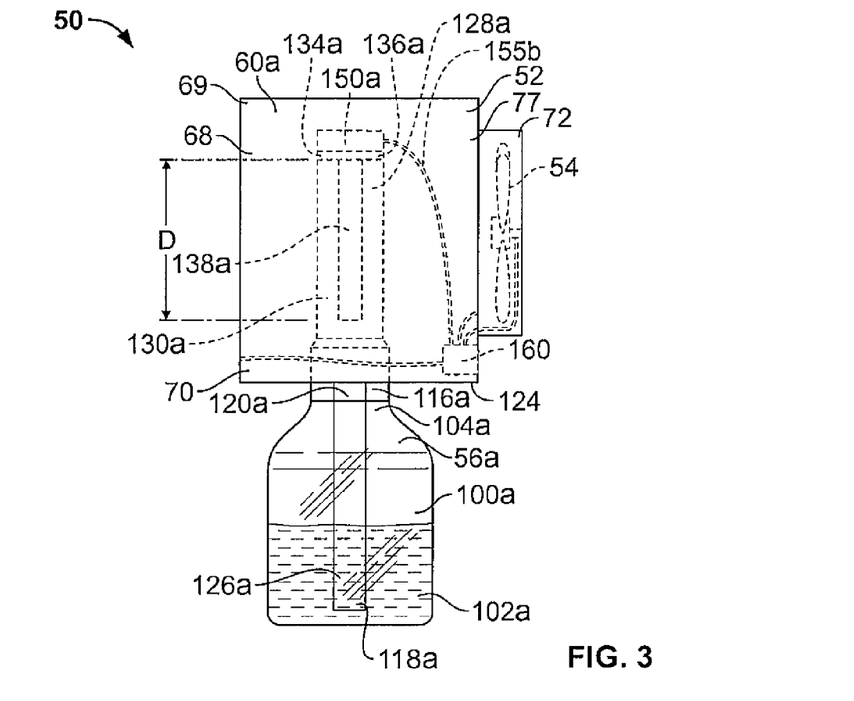
FIG. 3 is a side elevational view of the apparatus of FIG. 1.

Referring to FIGS. 1, 2, 4, 7A, and 7B, the outlets 64a, 64b, are formed by shutters 66a, 66b that automatically open and close based on a program supplied by circuitry within the dispenser 50. The shutters 66a, 66b extend down a front portion 68 of the housing 52 and are associated with and operate in conjunction with the first and second chambers 60a, 60b. Any shutters or other members that can be automatically rotated, shifted, or otherwise moved to open and close the outlets 64a, 64b may alternatively be utilized. Further, the outlets 64a, 64b may be formed of any shape or size that facilitate transmission of volatile material therethrough. Internal surfaces 67a, 67b and/or external surfaces 73a, 73b (best seen in FIGS. 2 and 4) of the outlets 64a, 64b may also be coated with the material 61 that blocks fragrance absorption in a similar manner as described above with respect to the chambers 60a, 60b. In one example, the outlets 64a, 64b may be formed by vertical slits or openings and in another example, the outlets 64a, 64b may be formed by horizontal slits or openings. As seen in FIG. 1, the outlets 64a, 64b in the form of vertical slits extend completely from a top edge 69 to a bottom edge 70 of a front portion 71 of the housing 52. Alternatively, the slits may extend through only a portion of the front portion 68 of the housing 52. The outlets 64a, 64b are adapted to be automatically opened and closed to retain volatile materials inside the first and second chambers 60a, 60b, respectively, or to allow for the release of volatile materials from same. Illustratively, when the outlets 64a, 64b are closed, volatile material builds up inside of the chambers 60a, 60b and when the outlets 64a, 64b are open, volatile material escapes into the surrounding environment. The operation of the dispenser 50 and outlets 64a, 64b therefor will be discussed in greater detail hereinafter. As noted above, the shutters 66a, 66b are electrically connected to circuitry of any kind known in the art to allow for the automatic operation thereof according to one or a number of different programs, for example, those described hereinbelow.

The dispenser 50 further includes the fan 54, as shown in FIGS. 2-6, 7A, and 7B. The fan 54 may be replaced by two fans and/or any other air generating device including, but not limited to, an axial propeller-type fan, a centrifugal-type squirrel cage blower, a peristaltic pump, or any other fans or pumps known in the art. The outlets 64a, 64b allow airflow generated by the fan 54 to pass through the first and second chambers 60a, 60b, respectively, through the outlets 64a, 64b, and into the surrounding environment. The fan 54 is preferably positioned in a rear portion 72 of the housing 52 and preferably includes an airflow director 74 that controls the airflow from the fan 54. In particular, the airflow director 74 is positioned such that air is sent into only one of the chambers 60a, 60b of the housing 52 at a time. As shown in FIG. 7A, the airflow director 74 in the form of a door 76 slides from a first position, which allows airflow into the first chamber 60a and blocks airflow into the second chamber 60b (seen in FIG. 7A), to a second position, which allows airflow into the second chamber 60b and blocks airflow into the first chamber 60a. Optionally, the airflow generated by the fan 54 is not guided by an airflow director 74. Rather, as depicted in FIG. 7B, a plurality of louvers 75a, 75b cover inlets 76a, 76b that are positioned on an inner wall 77 disposed between the fan 54 and the first and second chambers 60a, 60b. The louvers 75a, 75b open and close to allow or prevent airflow between same. When the fan 54 is operational, first inlets 76a associated with the first chamber 60a may be opened such that airflow travels through the first inlets 76a and through the first chamber 60a. Similarly, second inlets 76b associated with the second chamber 60b are opened to allow airflow from the fan 54 to pass therethrough. The airflow director 74, movable louvers 75a, 75b, or other airflow directing or obstructing member are connected to circuitry within the dispenser 50 and are operated according to one or more programs to direct airflow, as discussed in greater detail hereinafter.

Figure 8:
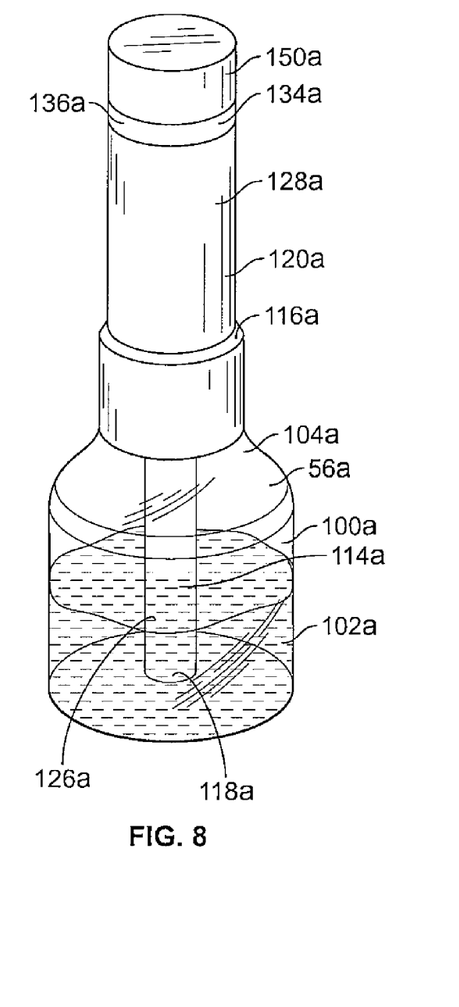
FIG. 8 is a top isometric view of a container for use in the apparatus of FIG. 1.
Figure 9:
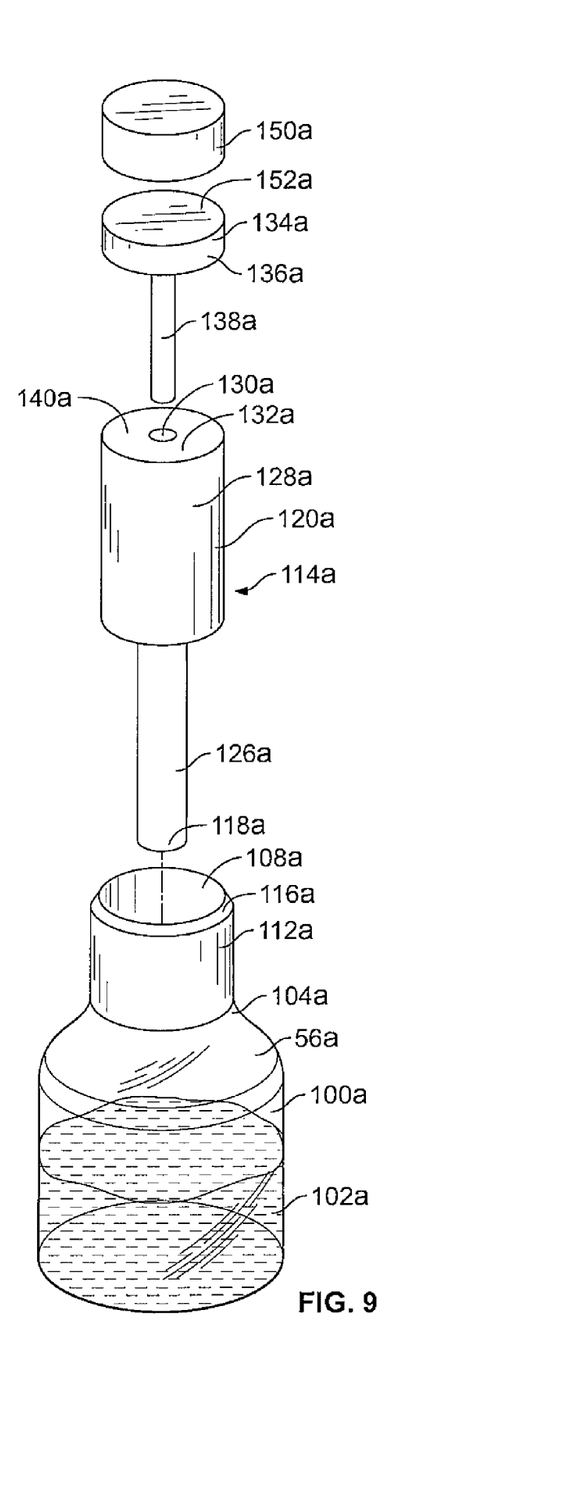
FIG. 9 is an exploded top isometric view of the container of FIG. 8.

As best seen in FIGS. 8 and 9, each container 56a, 56b of volatile material includes a body 100a, 100b having the volatile materials, in particular fragrances 102a, 102b, disposed therein. The containers 56a, 56b further include necks 104a, 104b extending upwardly from the bodies 100a, 100b, respectively, and apertures 108a, 108b disposed in distal ends 112a, 112b of the necks 104a, 104b, respectively. Wicks 114a, 114b are held within the containers 56a, 56b by locking rings 116a, 116b disposed in the necks 104a, 104b such that first ends 118a, 118b of the wicks 114a, 114b are disposed in the bodies 100a, 100b of the containers 56a, 56b in contact with the fragrances 102a, 102b and second ends 120a, 120b of the wicks 114a, 114b extend upwardly from the necks 104a, 104b out of the containers 56a, 56b. The containers 56a, 56b are adapted to be inserted into apertures 122a, 122b (FIG. 4) formed in a bottom portion 124 of the housing 52. The locking rings 116a, 116b preferably interact with the apertures 122a, 122b, such that the containers 56a, 56b may be inserted and retained within the housing 52. Optionally, the containers 56a, 56b may be held in the housing 52 in any manner known in the art, including an interference fit, a threaded screw, or the like. In addition, the fragrances 102a, 102b disposed in the containers 56a, 56b may be the same or different depending on the application.

Each wick 114a, 114b, as seen in FIGS. 8 and 9, includes a first section 126a, 126b in fluid communication with the fragrance 102a, 102b and a second section 128a, 128b disposed adjacent the first section 126a, 126b and extending out of the container 56a, 56b through the respective locking ring 116a, 116b. The wicks 114a, 114b are shown as substantially cylindrical in cross-section. Alternatively, the wicks 114a, 114b may be formed of other shapes, as desired. As shown in FIGS. 3, 7A, 7B, 8, and 9, a diameter of each first section 126a, 126b is less than a diameter of each second section 128a, 128b. The second sections 128a, 128b of each wick 114a, 114b, respectively, further include channels 130a, 130b disposed through top portions 132a, 132b thereof as best seen in FIG. 9. Inserts 134a, 134b having cylindrical ends 136a, 136b and downwardly extending posts 138a, 138b (FIG. 9) are inserted into and retained within each channel 130a, 130b such that the posts 138a, 138b are disposed within and surrounded by the respective second sections 128a, 128b and the cylindrical ends 136a, 136b rest on and substantially cover top surfaces 140a, 140b of the respective second sections 128a, 128b of each wick 114a, 114b. The inserts 134a, 134b are preferably made of a heat conductive material, such as aluminum. Other materials may also be suitable including steel, carbon fibers, other metals, polymers, and/or blends of any of the aforementioned. Preferably, a heat conducting material is selected such that heat may be conducted uniformly through a large portion of each second section 128a, 128b. The inserts 134a, 134b are preferably formed of the same material, but optionally, may be formed of different materials.

Referring to FIGS. 3, 4, 7A, 7B, 8, and 9, heaters 150a, 150b are adapted to be used with each wick 114a, 114b to facilitate the release of the fragrance 102a, 102b therefrom. When the containers 56a, 56b are inserted into the housing 52, the heaters 150a, 150b are disposed on and substantially cover upper surfaces 152a, 152b of the inserts 134a, 134b. The heaters 150a, 150b transmit heat directly to the inserts 134a, 134b, respectively, which is thereby transferred by conduction throughout the second sections 128a, 128b of the wicks 114a, 114b. The heaters 150a, 150b may be any shape and/or size, but preferably are manufactured to have a similar diameter as that of the second sections 128a, 128b. A heater 150a, 150b may be supplied with each container 56a, 56b, wick 114a, 114b, and insert 134a, 134b as part of a refill package. In this case, the heaters 150a, 150b may include a timing device and/or power source that allows the heater 150a, 150b to operate according to a program independently from the volatile material dispenser 50. Alternatively, the heaters 150a, 150b may be disposed within the housing 52 of the dispenser 50, for example as seen in FIG. 4, the heaters 150a, 150b may be held by rigid wires 151a, 151b or another structure that extends from a wall 153 within the housing 52. Electrical wires 155a, 155b extend from a circuit board (not shown) to the heaters 150a, 150b, respectively, and may extend over the rigid wires 151a, 151b or other similar structure. In this case, each container 56a, 56b, wick 114a, 114b, and insert 134a, 134b is sold as a refill unit. Each wick insert 134a, 134b may include a mechanism to allow the insert 134a, 134b to position and/or attach to the heater 150a, 150b once each container 56a, 56b, wick 114a, 114b, and insert 134a, 134b combination is inserted in the housing 52. Any such mechanism known in the art may be used to facilitate the positioning and/or attachment thereof including snap-fit, snug fit, magnets, or the like.

Figure 5:
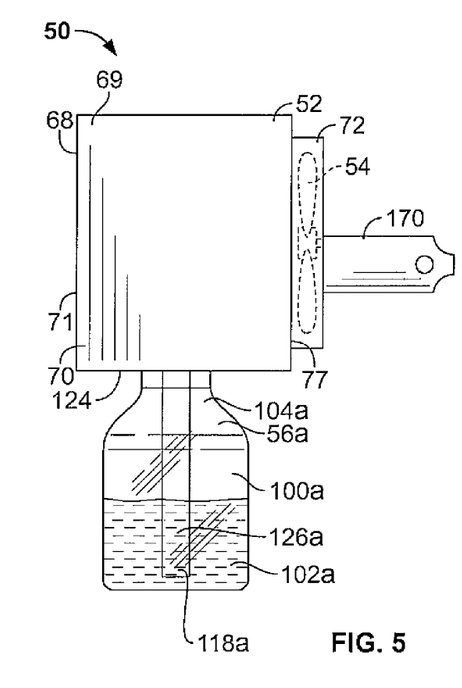
FIG. 5 is a side elevational view of the apparatus of FIG. 1 with electrical prongs for powering the apparatus.

A controller 160, which is implemented by circuitry such as an application specific integrated circuit (ASIC) or a microcontroller, is disposed within the housing 52 and is adapted to control the fan 70, the heaters 150a, 150b, the shutters 66a, 66b, and/or the airflow director 74. The controller 160 is electrically connected to each of the individual aforementioned components. Further, as seen in FIG. 6, a compartment 165 is disposed within the housing 52, wherein the compartment 165 holds standard batteries 167 to supply power to the controller 160 and other components of the dispenser 50. Alternatively, as seen in FIG. 5, electrical prongs 170 may extend from the housing 52 and connect the dispenser 50 to an external power source. The dispenser 50 may further include a user-interface disposed on the housing 52 such that a user can adjust the settings of the dispenser 50 and control the operation thereof as described in more detail below.

Several modes of operating the dispenser 50 while inhibiting habituation and/or adaptation with regard to fragrances are included in this disclosure.

In a first mode 200 of dispensing, as seen in FIGS. 10-13, two or more fragrances are alternatingly heated and dispensed. In one illustrative example implementing the first mode 200 of dispensing and referring to FIG. 10, initially, the fan 70 is in the off position and the shutters 66a, 66b are in a closed position such that airflow through the outlets 64a, 64b does not occur. A first heater 150a associated with the first wick 114a is activated for a time period between $t_0$ and $t_1$. During this heating step, the first fragrance 102a is volatilized at an increased rate as compared to volatilization that takes place at room temperature. Since the fan 70 is not operating and the shutters 66a are closed, the first fragrance 102a fills and remains contained within the first chamber 60a. At time $t_1$, the first heater 150a is deactivated, the fan 70 is energized, the airflow director 74 is adjusted such that airflow from the fan 70 is directed toward the first chamber 60a, and the shutters 66a associated with the first chamber 60a are opened. Airflow from the fan 70 moves through the first chamber 60a and through the outlet 64a into the surrounding environment with fragrance therein for the time period between $t_1$ and $t_2$. At time $t_2$, the fan 70 is deactivated, the shutters 66a are closed to substantially seal the first chamber 60a from the surrounding environment, and the heater 150b is activated. During the time period between $t_2$ and $t_3$, the second fragrance 102b is volatilized at an increased rate as compared to volatilization that takes place at room temperature. The second fragrance 102b fills and remains contained within the second chamber 60b. At time $t_3$, the second heater 150b is deactivated, the fan 70 is energized, the airflow director 74 is adjusted such that airflow from the fan 70 is directed toward the second chamber 60b, and the shutters 66b associated with the second chamber 60b are opened. During the time period between $t_3$ and $t_4$, airflow from the fan 70 moves through the second chamber 60b and through the outlet 64b into the surrounding environment with fragrance therein. After emission of the second fragrance 102b, the process repeats starting at time $t_4$. This process can be repeated any number of times or continuously (until the dispenser is deactivated). Optionally, a rest time period between $t_4$ and $t_5$ may be included following the emission of the second fragrance 102b and before the next emission of the first fragrance 102a. The rest time period allows a gap, wherein the outlets 64a, 64b are closed, the fan 70 and heaters 150a, 150b are off, and substantially no fragrance is emitted into about 1 hour.

Figure 10:
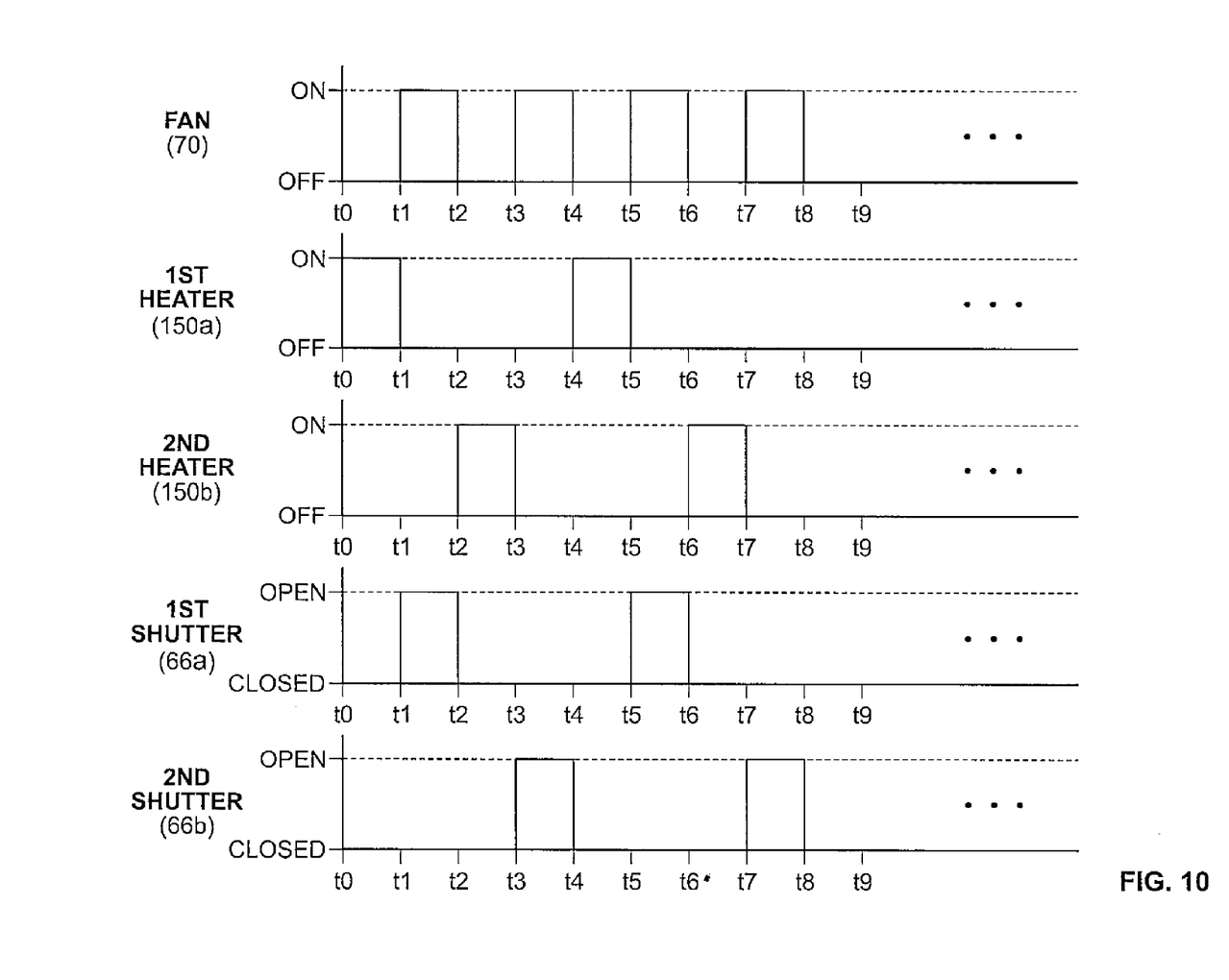
FIGS. 10-14 are diagrammatic representations of modes of operation for heaters, shutters, and a fan for any of the volatile material dispensing apparatuses disclosed herein.

In the first mode 200 of dispensing, the heating time periods between $t_0$ and $t_1$ and between $t_2$ and $t_3$ are preferably between about 1 minute and about 3 hours, more preferably between about 20 minutes and about 1 hour, and most preferably about 30 minutes. The dispensing time periods between $t_1$ and $t_2$ and between $t_3$ and $t_4$ when the fan 70 is activated and the one set of shutters 66a, 66b are open, are preferably between about 1 second and about 1 hour, more preferably between about 10 seconds and about 10 minutes, and most preferably about 30 seconds. The time periods between $t_0$ and $t_1$ and between $t_2$ and $t_3$ are approximately equal to each other and the time periods between $t_1$ and $t_2$ and between $t_3$ and $t_4$ are approximately equal to each other. Optionally, the time periods between $t_0$ and $t_1$ and between $t_2$ and $t_3$ are different from each other and/or the time periods between $t_1$ and $t_2$ and between $t_3$ and $t_4$ are different from each other.

Figure 11:
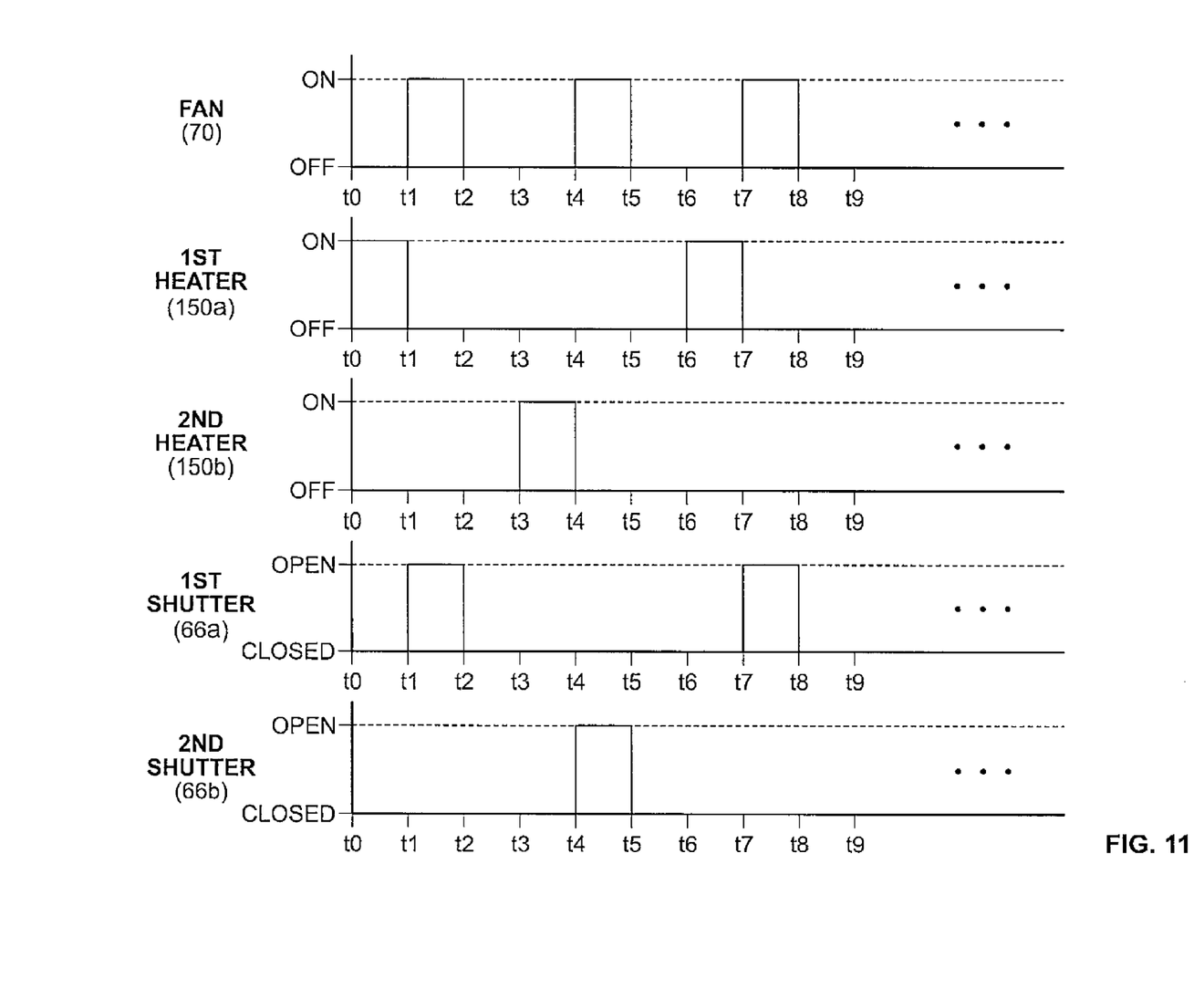
Figure 12:
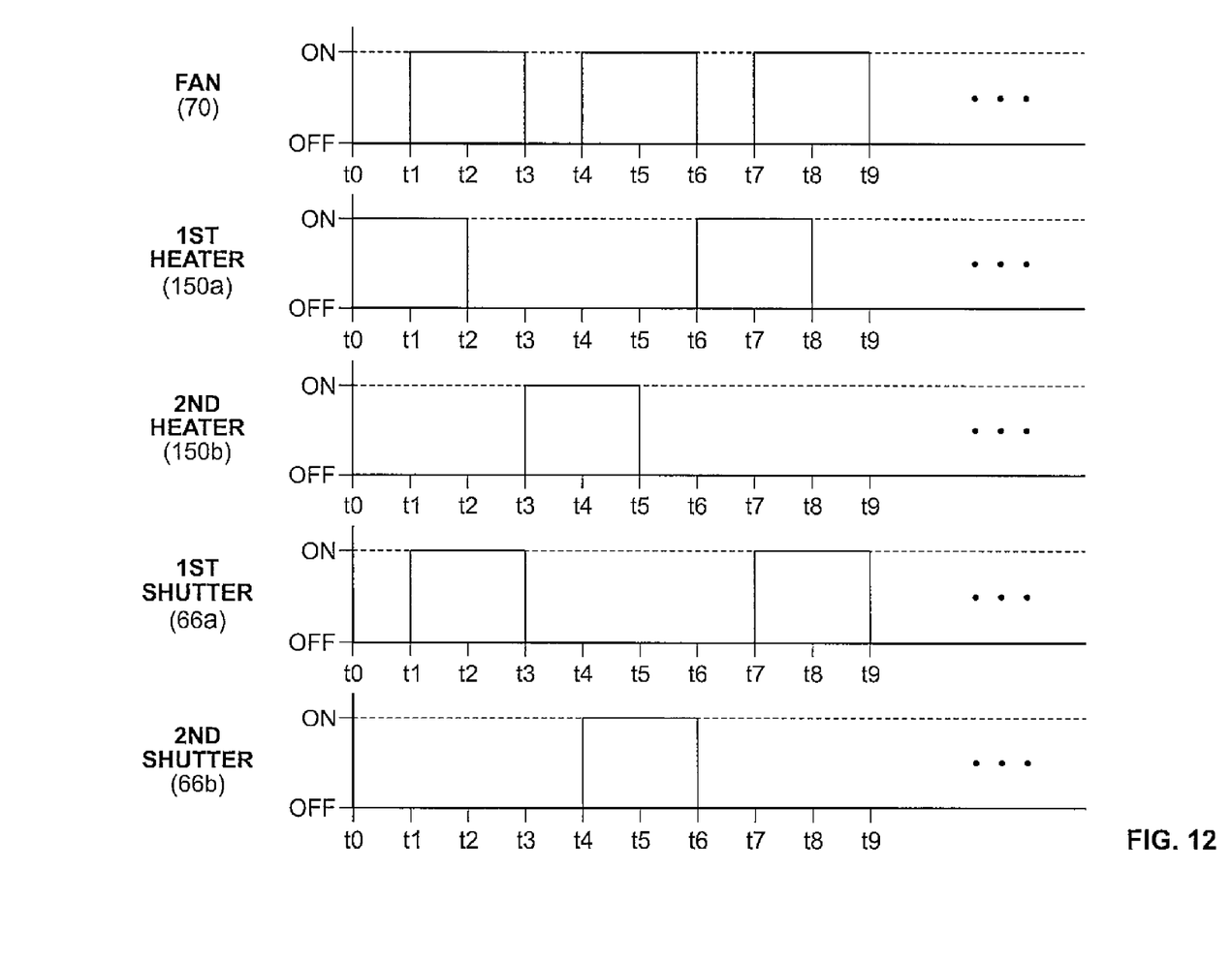

Still referring to FIG. 10, the activation/deactivation of the fan 70 may occur simultaneously with the opening/closing of the shutters 66a, 66b, and/or activation/deactivation of the heaters 150a, 150b. Alternatively, as shown in FIG. 11, the heaters 150a, 150b may be activated after a period of time, such as the time period between $t_2$ and $t_3$ and between $t_5$ and $t_6$, after the fan 70 has been deactivated and the opposite shutters 66a, 66b have been closed. Still further, as seen in FIG. 12, the activation of the fan 70 and the opening of one set of shutters 66a, 66b may occur before deactivation of the other of the heaters 150a, 150b. Any of the previously described time periods may overlap to some degree or may be switched as desired.

Figure 13:
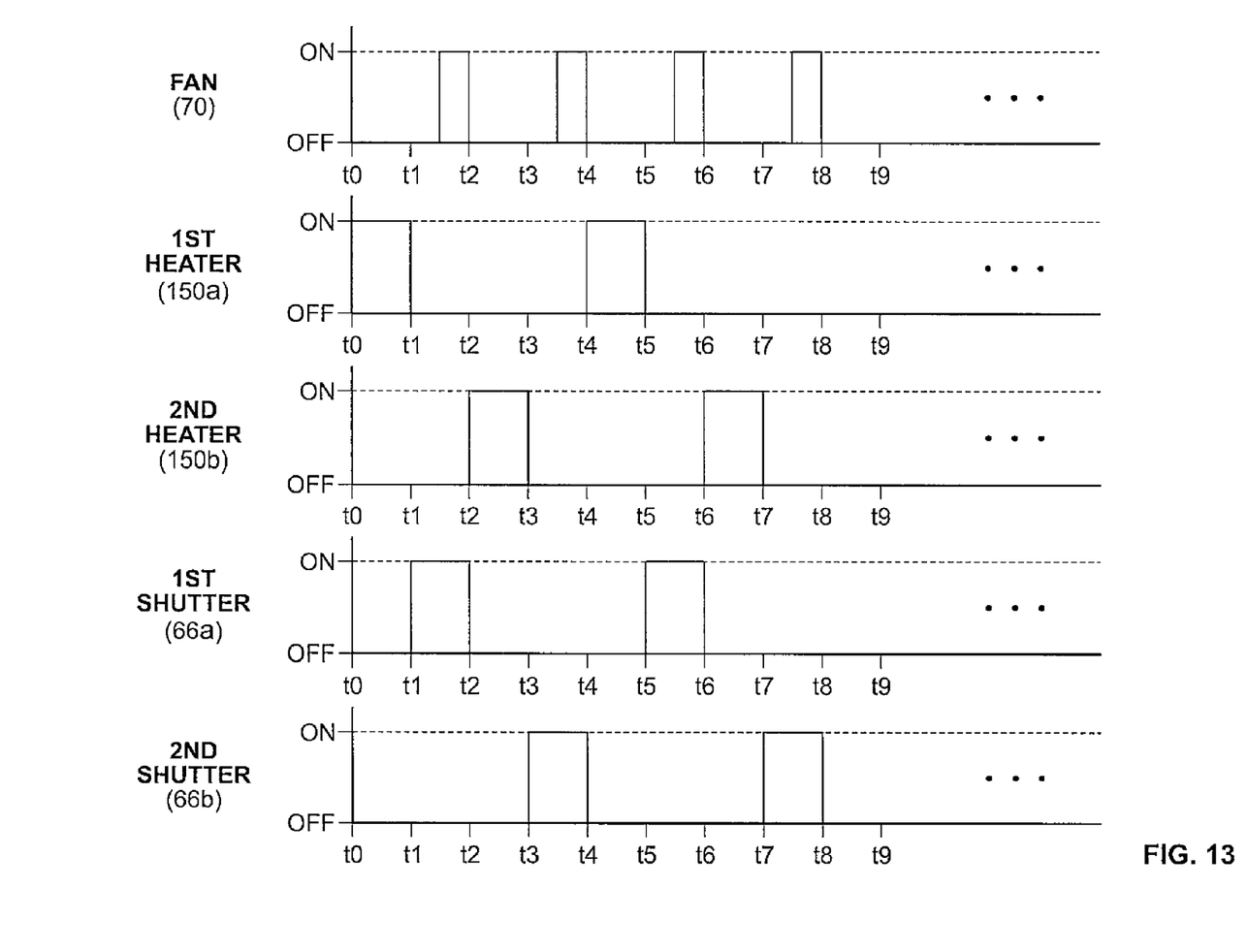

A second mode of operation, as shown in FIG. 13, is similar to that of FIG. 10, except that the fan 70 is activated for a shorter period of time with respect to the period of time that the shutters 66a, 66b are in the open position. It is believed that the shortened time period for activation of the fan 70 allows for efficient power-use in the dispenser 50, which in turn allows the dispenser 50 to be battery-operated. In all of the modes of operation disclosed herein, the activation time period for the fan 70 and/or heaters 150a, 150b can be adjusted to decrease power consumption. As with the modes of operation described above, gaps or overlaps may be incorporated into the mode of operation of FIG. 13.

Figure 14:
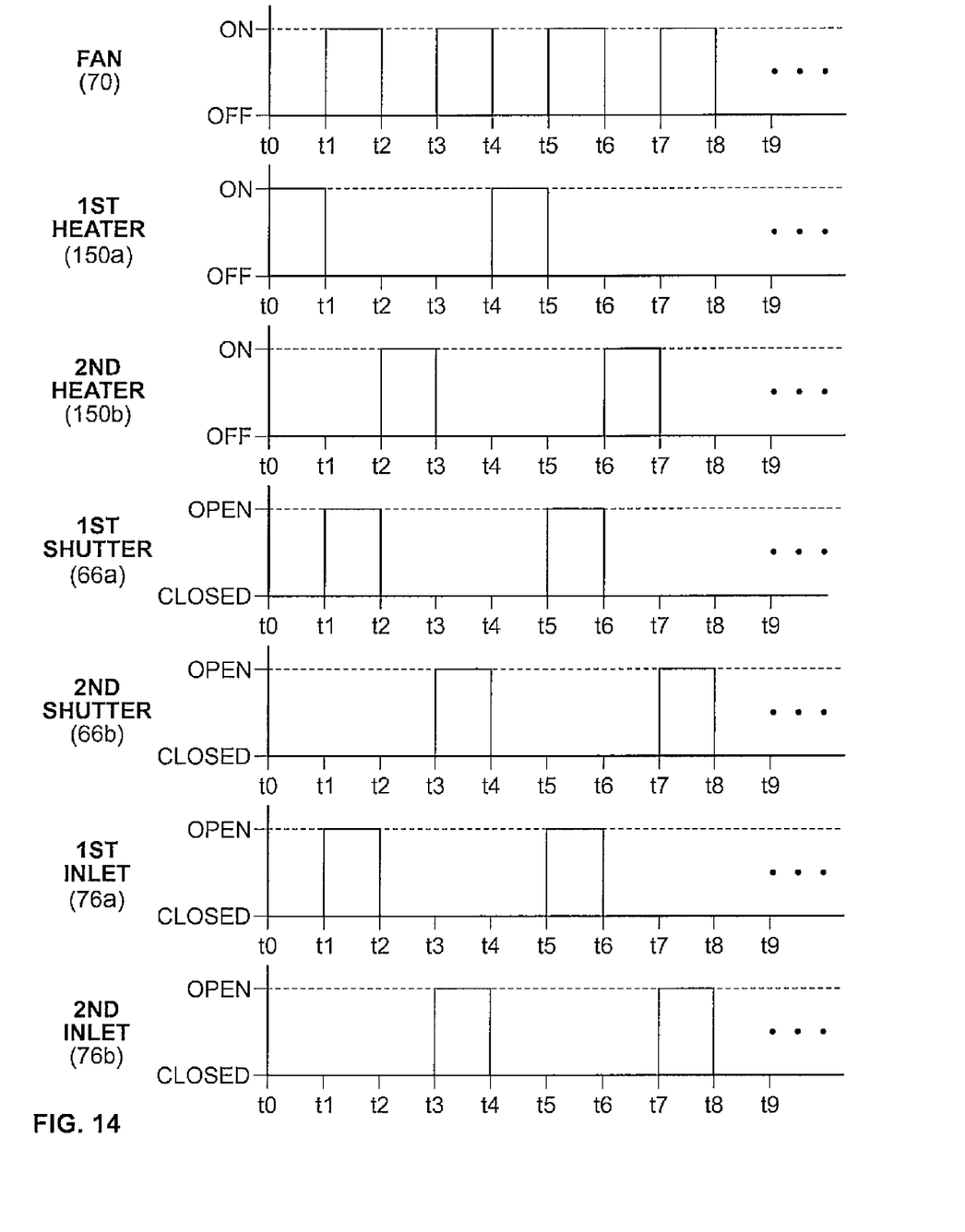

In a further mode of operation, as seen in FIG. 14, the louvers 75a, 75b or door 76 operate in conjunction with the fan 70a, the heaters 150a, 150b, and the shutters 66a, 66b to allow or prevent airflow therethrough. In particular, the louvers 75a, 75b, would be opened or closed to open or close the inlets 76a, 76b in conjunction with the associated shutters 66a, 66b to allow airflow through the chambers 60a, 60b in the same manner and at the same time as the shutters 66a, 66b, respectively. If a door 76 is utilized, the door 76 would be moved in conjunction with the shutters 66a, 66b to open or close the inlets 76a, 76b.

The controller 160 optionally includes an internal clock or timer to allow the dispenser to activate the heaters 150a, 150b, the fan 70, the shutters 66a, 66b, the louvers 75a, 75b and/or the door 76 at the appropriate time intervals. It is contemplated that such an internal clock or timer could be realized by inclusion of light sensors and/or appropriate software or firmware. It is further contemplated that an internal clock may be a variety of "atomic clock" that links by radio signal to synchronize with an official clock, for example, the official U.S. atomic clock located in Boulder, Colo.

The present disclosure is directed to an apparatus and method for dispensing volatile materials that increase a user's perception of the dispensed volatile materials. While specific embodiments are discussed herein, it is understood that the present disclosure is to be considered only as an exemplification of the principles of the present disclosure. For example, lengths of time periods as disclosed for each of the modes of dispensing hereinabove are approximate and may not be absolute but rather may be intended to impart the relative lengths of the time periods with respect to one another.

Further, although the apparatuses and modes of dispensing disclosed herein refer to fragrances rather than volatile materials, it is to be understood that any type of volatile material may be utilized with any of the apparatuses and modes of dispensing as disclosed herein. Illustratively, the types of volatile materials may be, for example, a disinfectant, a mold or mildew inhibitor, a fragrance, a disinfectant, an air purifier, an aromatherapy scent, an antiseptic, an odor eliminator, a positive fragrancing active material, an air-freshener, a deodorizer, or the like, and combinations thereof.

INDUSTRIAL APPLICABILITY

Methods of dispensing a volatile material and an apparatus for executing the methods of dispensing while inhibiting adaptation and/or habituation in response to the volatile material have been presented. The apparatus includes a housing having a fan, two or more chambers, containers containing fragrances disposed within each of the chambers, and shutters associated with the chambers. The method generally includes heating the fragrance while the outlet is in a closed position and activating a fan and associated outlets to facilitate the release of the volatile active from the dispenser.

Numerous modifications to the present disclosure will be apparent to those skilled in the art in view of the foregoing description. Accordingly, this description is to be construed as illustrative only and is presented for the purpose of enabling those skilled in the art to make and use the disclosure and to teach the best mode of carrying out same. The exclusive right to all modifications within the scope of the impending claims is expressly reserved. All patents, patent publications and applications, and other references cited herein are incorporated by reference herein in their entirety.

We claim:

1. An apparatus for dispensing a volatile active into the surrounding environment, comprising:
   a housing having first and second chambers;
   a fan disposed within the housing;
   an airflow director disposed adjacent the fan for directing airflow into only one of the first or second chambers at a time;
   first and a second containers having first and second fragrances disposed therein and first and second wicks in communication with the first and second fragrances and extending into the first and second chambers, respectively, wherein first and second inserts are disposed in central portions of the first and second wicks, respectively; and
   first and second heaters disposed adjacent the first and second inserts to transfer heat to the first and second inserts, respectively.

2. The apparatus of claim 1, further including first and second outlets associated with the first and second chambers, respectively, wherein shutters are associated with each of the first and second outlets to open and close same.

3. The apparatus of claim 1, wherein the airflow director comprises a slidable shield that is movable from a first position that directs airflow into the first chamber and blocks airflow into the second chamber, to a second position that directs airflow into the second chamber and blocks airflow into the first chamber.

4. The apparatus of claim 1, wherein the inserts comprise a heat conductive material.

5. The apparatus of claim 4, wherein the heaters are disposed on a top wall of the housing and releasably engage the inserts when the containers are inserted into the housing.

6. The apparatus of claim 1, wherein the airflow director comprises a plurality of louvers covering inlets positioned on an inner wall disposed between the fan and the first and second chambers, wherein the louvers open and close to allow or prevent airflow between same.

7. The apparatus of claim 1, wherein each of the inserts includes a cylindrical end adjacent an end of each wick and a post extending away from the cylindrical end and into a channel formed within a respective wick.

8. The apparatus of claim 7, wherein the heaters are disposed adjacent the cylindrical ends of the inserts.

9. An apparatus for dispensing a volatile active into the surrounding environment, comprising:
   a housing having first and second chambers;
   a fan disposed within the housing;
   first and a second containers having first and second fragrances disposed therein and first and second wicks in communication with the first and second fragrances and extending into the first and second chambers, respectively, wherein first and second inserts are disposed in central portions of the first and second wicks, respectively; and
   first and second heaters disposed adjacent the first and second inserts to transfer heat to the first and second inserts, respectively.

10. The apparatus of claim 9, further including first and second outlets associated with the first and second chambers, respectively, wherein shutters are associated with each of the first and second outlets to open and close same.

11. The apparatus of claim 9, wherein the inserts comprise a heat conductive material.

12. The apparatus of claim 11, wherein the heaters are disposed on a top wall of the housing and releasably engage the inserts when the containers are inserted into the housing.

13. The apparatus of claim 9, wherein each of the inserts includes a cylindrical end adjacent an end of each wick and a post extending away from the cylindrical end and into a channel formed within a respective wick.

14. The apparatus of claim 13, wherein the heaters are disposed adjacent the cylindrical ends of the inserts.

15. An apparatus for dispensing a volatile active into the surrounding environment, comprising:
   a housing;
   a fan disposed within the housing;
   a container having a fragrance disposed therein and a wick in communication with the fragrance, wherein an insert is disposed in central portions of the wick; and
   a heater disposed adjacent the insert to transfer heat to the insert.

* * * * *